United States Patent [19]

Haynie

[11] 4,166,468

[45] Sep. 4, 1979

[54] APPARATUS FOR ENDOTRACHEAL AND ESOPHAGEAL INTUBATION

[76] Inventor: Louis D. Haynie, 215 Mulberry Pl., Birmingham, Ala. 35214

[21] Appl. No.: 822,136

[22] Filed: Aug. 5, 1977

[51] Int. Cl.² .......................................... A61M 25/00
[52] U.S. Cl. ................................ 128/351; 128/349 B
[58] Field of Search .................. 128/348, 350 R, 351, 128/208, 349 B, 349 BV

[56] References Cited

U.S. PATENT DOCUMENTS

| 3,331,371 | 7/1967 | Rocchi et al. | 128/349 B |
| 3,392,722 | 7/1968 | Jorgensen | 128/350 R X |
| 3,395,710 | 8/1968 | Stratton et al. | 128/350 R |
| 3,599,642 | 8/1971 | Tindel | 128/351 |
| 3,874,377 | 4/1975 | Davidson | 128/351 X |

*Primary Examiner*—Dalton L. Truluck
*Attorney, Agent, or Firm*—Woodford R. Thompson, Jr.

[57] ABSTRACT

Apparatus for endotracheal and esophageal intubation embodying an elongated tubular member having a first portion with an open outer end and a second portion with an open inner end and a lumen extending therebetween. A first inflatable member is carried about the second portion of the tubular member for inflation within a body canal to form a seal with the walls thereof. A second inflatable member within the lumen seals the lumen when inflated and an air control unit between the outer end of the tubular member and the second inflatable member selectively communicates the lumen with the exterior of the first portion.

2 Claims, 7 Drawing Figures

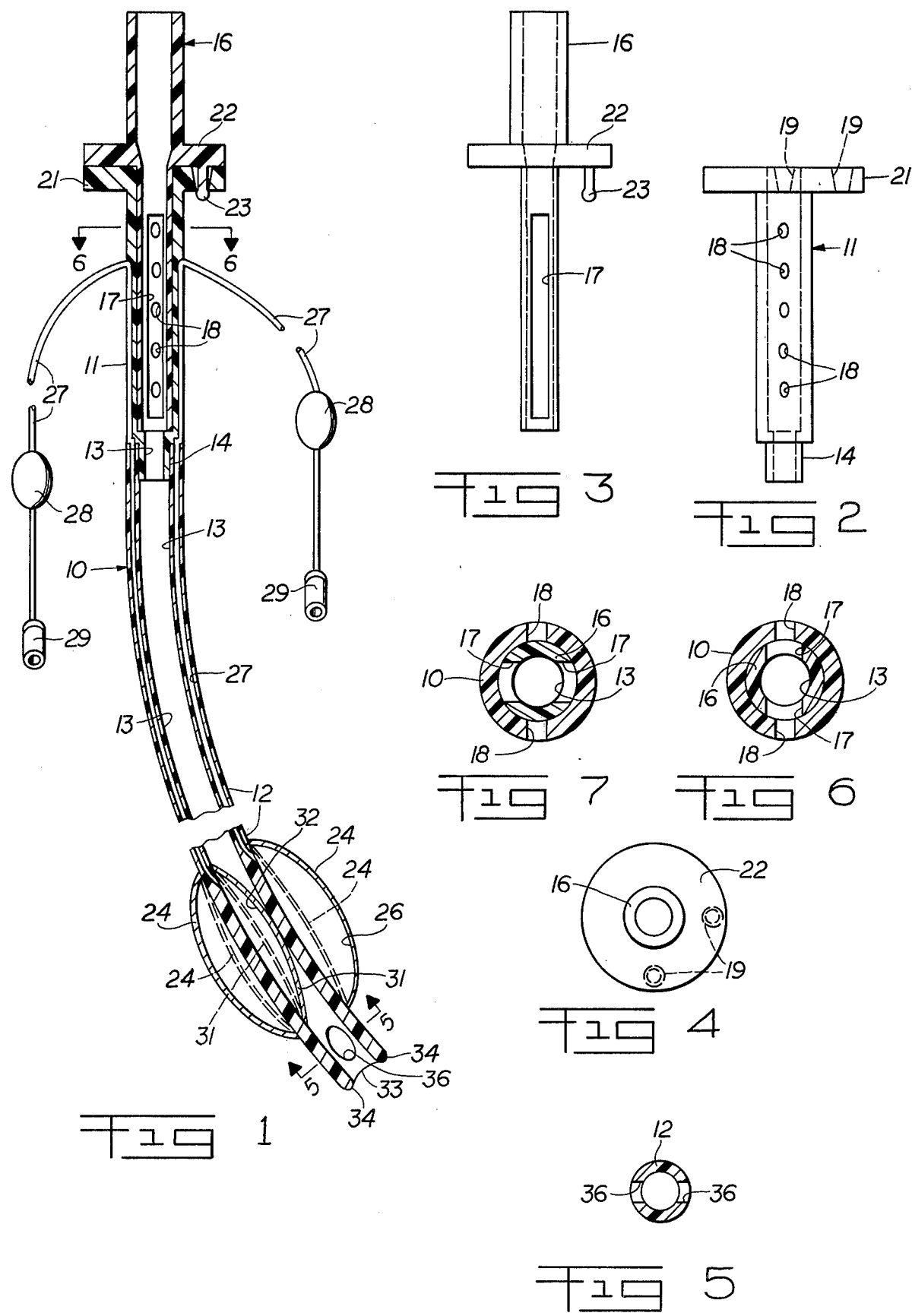

4,166,468

APPARATUS FOR ENDOTRACHEAL AND ESOPHAGEAL INTUBATION

BACKGROUND OF THE INVENTION

This invention relates to apparatus for endotracheal and esophageal intubation and more particularly to such apparatus which is adapted to establish an airway rapidly in a patient regardless of whether or not the air way is initially established to the trachea or to the esophagus.

Heretofore in the art to which my invention relates, difficulties have been encountered in establishing an airway rapidly in a patient under emergency conditions due to the fact that the airway is sometimes initially established to the esophagus rather than to the trachea whereby the apparatus must be removed and reinserted or the passageway to the esophagus must be closed to prevent air from being forced into the stomach and also to prevent regurgitation. Where the passageway to the esophagus is closed, other means must be provided for communicating the apparatus with the trachea, such as by providing passageways in the upper portion of the apparatus which may be open at the time the passageway into the esophagus is closed. The Kenneth L. Davidson U.S. Pat. No. 3,874,377 shows apparatus wherein an adaptor is inserted into an elongated tubular member whereby a portion of the tubular member is sealed upon insertion of the adaptor into the tubular member or upon rotation of components of the adaptor relative to each other to close a portion of the elongated tube. The insertion of such adaptors or the movement of one portion of the adaptor relative to another after insertion into the patient is very difficult and requires a considerable amount of time. Also, it is difficult to determine positively whether or not the passageway to the esophagus has been closed. The patents to Schossow U.S. Pat. No. 3,087,493 and Doherty U.S. Pat. No. 3,460,541 also show conventional types of endotracheal tubes.

SUMMARY OF THE INVENTION

In accordance with my invention, I provide apparatus which may be employed either for endotracheal or esophageal intubation whereby an air passageway is provided to the trachea in the event the initial air passageway is established to the esophagus rather than to the trachea. On the other hand, when the initial air passageway is established to the trachea, the apparatus is adapted for direct endotracheal intubation. Accordingly, a single tube performs the function of two tubes due to the fact that means is provided for communicating the elongated tube with the trachea whether the initial air passageway is established to the trachea or the esophagus.

My improved apparatus embodies an elongated tubular member having a first portion with an open outer end and a second portion with an open inner end and a lumen extending therebetween. A first inflatable member surrounds the outer walls of the second portion of the tubular member in spaced relation to the inner end thereof for inflation within a body canal to form a seal. A second inflatable member is mounted within the lumen of the tubular member for sealing the lumen when inflated. Means is provided between the outer end of the tubular member and the second inflatable member for selectively communicating the lumen of the tubular member with the exterior portion thereof so that the apparatus is adapted for endotracheal intubation when the lumen is open for fluid communication between the outer and inner ends of the tubular member and is not in communication with the exterior surface of the upper portion of the tubular member. The apparatus is adapted for esophageal intubation when the second inflatable member is inflated to seal the lumen and the lumen is in fluid communication with the exterior of the tubular member to thus supply air to the trachea.

DESCRIPTION OF THE DRAWING

Apparatus embodying features of my invention is illustrated in the accompanying drawing, forming a part of this application, in which:

FIG. 1 is a longitudinal sectional view showing the components of my improved apparatus in position for esophageal intubation;

FIG. 2 is a side elevational view showing the upper portion of the elongated tubular member with the components thereof in the position shown in FIG. 1;

FIG. 3 is a side elevational view showing an insert which is adapted to telescope within the upper portion of the tubular member shown in FIG. 2 for selectively communicating the lumen of the elongated tubular member with the exterior thereof;

FIG. 4 is an end elevational view showing the outer end of the apparatus with the insert attached to the upper portion of the elongated tubular member;

FIG. 5 is a sectional view taken generally along the line 5—5 of FIG. 1;

FIG. 6 is a sectional view taken generally along the line 6—6 of FIG. 1; and,

FIG. 7 is a sectional view corresponding to FIG. 6 but showing the insert rotated 90° from the position shown in FIG. 6 whereby the apparatus is adapted for endotracheal intubation.

DETAILED DESCRIPTION

Referring now to the drawing for a better understanding of my invention, I show an elongated tubular member 10 having a first portion 11 with an open outer end and a second portion 12 with an open inner end, as shown. A lumen 13 extends between the outer and inner ends of the elongated tubular member 10, as clearly shown in FIG. 1. Preferably, the first portion 11 of the elongated tubular member 10 is generally cylindrical in shape and is provided with a reduced diameter portion 14 which is of a size to telescope into the open end of an elongated flexible tube, as shown, which provides the second portion 12.

Telescoping downwardly within the outer portion 11 is a tubular insert 16 having an elongated, longitudinally extending slot 17 therethrough which is adapted to move into alignment with and into communication with longitudinally aligned openings 18 provided in the upper portion 11 of the elongated tubular member 10 whereby the lumen 13 is adapted to communicate with the exterior of the upper portion 11. Upon rotation of the insert 16 90° from the position shown in FIG. 6, the insert 16 is rotated to the position shown in FIG. 7 whereby the elongated slot 17 moves out of alignment with the openings 18 whereby the lumen 13 of the elongated tubular member 10 no longer communicates with the exterior portion thereof.

To lock the insert 16 selectively in the position shown in FIGS. 6 and 7, angularly spaced recesses 19 are provided in a lateral, annular flange 21 provided at the outer end of the outer portion 11. As shown in FIGS. 1 and 3, a lateral, annular flange 22 is carried by the insert 16 in position to engage the annular flange 21 when moved to the position shown in FIG. 1. A depending projection 23 is carried by the lateral flange 22 in position to engage selectively the recesses 19 provided in the lateral flange 21. Accordingly, to detachably attach the insert 16 to the upper portion 11 of the elongated tubular member 10, the insert 16 is moved downwardly whereby the projection 23 snaps into a selected one of the recesses 19 to thus retain the insert 16 in either the position shown in FIG. 6 or the position shown in FIG. 7.

A first inflatable member 24 is carried about the outer walls of the second portion 12 of the elongated tubular member 10 in spaced relation to the inner end thereof for inflation within a body canal to form a seal with the walls thereof. That is, the inner end of the second portion 12 of the elongated tubular member 10 is adapted to enter the trachea or the esophagus of a patient and after insertion therein, the inflatable member 24 is inflated to form a seal between the portion 12 of the elongated tubular member 10 and the trachea or the esophagus, as the case may be. The inflatable member 24 is shown as being secured at its upper and lower ends to the outer surface of the portion 12 of the elongated tubular member 10 to form a cavity 26 between the inflatable member 24 and the outer surface of the portion 12 whereby the inflatable member 24 is adapted to move from the inflated or solid line position to the deflated or dotted line position. An air tube 27 communicates with the cavity 26, as shown in FIG. 1 whereby air may be introduced into or exhausted from the inflatable member 24. The air passageway 27 may be in the form of a small tubular member which extends outwardly of the elongated tubular member 10 and is connected to a pilot bult 28 which indicates inflation or deflation of the inflatable member 24. An elongated groove is provided in the outer surface of the side wall of the outer portion 11 for receiving the tube 27 whereby the tube 27 is concealed at the point it passes the mouth area of the patient, thus preventing damage to the tube by the teeth of the patient. The air tube 27 preferably extends through the pilot bult 28 and is in communication therewith with the outer end of the tubular member 27 being attached to a conventional releasable, check valve 29 which permits the inflatable member 24 to be inflated or deflated by employing a conventional syringe or the like. In view of the fact that the pilot bulb 28 and the means 29 for introducing and exhausting air from the tube 27 are conventional and other suitable means may be employed, no further description thereof is deemed necessary.

As shown in FIG. 1, a second inflatable member 31 is mounted within the lumen 13 of the portion 12 of the elongated tubular member 10 for sealing the lumen when inflated. The inflatable member 31 is shown as being a balloon-like member mounted adjacent the inner surface of the lumen 13 in position to extend alongside the inner wall surface of the lumen when deflated to the dotted line position shown in FIG. 1. Accordingly, while the inflatable member 31 is in the solid line position, it closes the lumen 13 whereby air cannot pass through the portion 12 of the elongated member 10. On the other hand, upon deflating the inflatable member 31, the member 31 moves to the dotted line position alongside the inner wall of the lumen 13 to thus permit free passageway of air through the lumen of the elongated member 10. The inflatable member 31 is provided with a cavity 32 therein which communicates with an air tube 27, as described hereinabove. That is, the air tube 27 extends outwardly of the elongated tubular member 10 and carries a pilot bulb 28. Also, the free end of the tubular member 27 communicates with a releasable valve member 29 which permits introducing air into the inflatable member 31 or exhausting air therefrom.

As shown in FIG. 1, the inner end of the portion 12 of the tubular member 10 is generally concave as at 33, as viewed in side elevation, with the juncture of the outer side of the portion 12 of the tubular member 10 and the inner end of the portion 12 being rounded as at 34 whereby there is a minimum injury to the air passages of the patient as the apparatus is inserted or removed from the patient. As shown in FIGS. 1 and 5 the portion 12 of the tubular member 10 is provided with oppositely disposed passageways 36 in its walls adjacent and inwardly of the inner end thereof so that one opening 36 will remain open in the event the other opening 36 should be in engagement with a body canal, such as the trachea or the esophagus.

The outer end of the upper portion 11 of the tubular member 10 is connected to a suitable source of air, not shown. In view of the fact that the means for supplying air to and exhausting air from such apparatus is well known in the art to which my invention relates, no further description thereof is deemed necessary.

From the foregoing description, the operation of my improved apparatus will be readily understood. The insert 16 is inserted into the open outer end of the portion 11 of the elongated tubular member 10, as shown in FIG. 1, in either the esophagus position shown in FIG. 6 or the trachea position shown in FIG. 7. That is, in the esophagus position, the elongated slot 17 is in alignment and communicates with the openings 18 in the portion 11 of the elongated tubular member 10 whereby the lumen 13 of the upper portion 11 communicates with the exterior of the outer portion 11. The insert 16 is detachably secured to the upper portion 11 of the elongated member 10 by pressing downwardly on the insert 16 whereby the projection 23 snaps into the selected opening 19 to hold the insert in either the position shown in FIG. 6 or the position shown in FIG. 7. In the position shown in FIG. 7, the elongated slots 17 are moved out of alignment with the openings 18 whereby the lumen 13 of the outer portion 11 of the elongated member 10 is no longer in communication with the exterior of the portion 11.

In operation, the inner portion 12 of the elongated member 10 is inserted into the patient in an attempt to pass the inner end of the tubular member 10 into the trachea. In the event the inner end of the tubular member enters the trachea, the inflatable member 24 is inflated and the insert 16 is rotated to the position shown in FIG. 7, if it is not already in that position before insertion. Accordingly, air is free to pass directly through the elongated tubular member 10 to the trachea.

In the event the inner end of the elongated member 10 does not enter the trachea but enters the esophagus, the inflatable member 24 and the inflatable member 31 are both inflated whereby the lumen 13 is closed and the outer surface of the portion 12 of the elongated member 10 is sealed against the walls of the esophagus to thus avoid regurigation. The insert 16 is rotated to the position shown in FIG. 6, if it is not already in that position at the time of insertion whereby the elongated slot 17 moves into alignment with and communicates with the longitudinal lined openings 18 in the upper portion 11 of the tubular member 10. The air introduced into the lumen 13 of the portion 11 of the elongated tubular member 10 then passes outwardly through the openings 18 to the exterior of the portion 11 of the elongated tubular member 10 whereby the air then is introduced into the trachea or is exhausted therefrom through the aligned passageways 17 and 18.

To remove the apparatus from the patient, the inflatable member 24 is deflated whereby it moves to the dotted line position alongside the outer surface of the elongated tubular member 10.

From the foregoing, it will be seen that I have devised improved apparatus for both endrotracheal and esophageal intubation. By providing the inflatable member 31 within the lumen of the tubular member for sealing the lumen when inflated, I provide rapid means for establishing an airway and at the same time I eliminate regurigation since fluids from the stomach cannot pass outwardly through the tubular member 10. By providing the inflatable member 24 in combination with the inner inflatable member 31, my apparatus is particularly adapted for prolonged intubation due to the fact that there is a minimum of air passage to and from the stomach of the patient in the event the inner end of the tubular member enters the esophagus rather than the trachea. Also, by providing the insert 16 which permits selective communication of the lumen of the tubular member 10 with the exterior thereof, my improved apparatus is adapted to convey the air to the trachea through the aligned passageways 17 and 18 while the inflatable member 31 is inflated within the esophagus of a patient. Accordingly, successful insertion of my improved apparatus is accomplished regardless of whether or not the tubular member enters the esophagus or the trachea.

While I have shown my invention in but one form, it will be obvious to those skilled in the art that it is not so limited, but is susceptible of various changes and modifications without departing from the spirit thereof.

What I claim is:

1. Apparatus for endotracheal and esophageal intubation comprising:
   (a) an elongated tubular member having a first portion with an open outer end and a second portion with an open inner end and a lumen extending between said outer and inner ends,
   (b) a first inflatable member carried about the outer walls of said second portion of said tubular member in spaced relation to said inner end for inflation within a body canal to form a seal with the walls thereof,
   (c) a second inflatable member mounted within said lumen of said tubular member for sealing said lumen when inflated,
   (d) a plurality of discharge openings through the walls of said first portion of said tubular member between said outer end and said second inflatable member,
   (e) a tubular insert of a size to telescope into said open outer end of said first portion of said tubular member with one end of said insert projecting outwardly of said open outer end of said first portion,
   (f) at least one discharge opening through the walls of said insert in position to move into alignment and communication with said discharge openings in said first portion upon movement of said insert to one position and to move out of alignment and communication with said discharge openings in said first portion upon movement of said insert to another position,
   (g) a laterally extending flange carried by said first portion of said tubular member adjacent the outer open end thereof,
   (h) a laterally extending flange carried by said insert in position to extend alongside said flange carried by said first portion, and
   (i) a projection carried by one laterally extending flange and angularly spaced recesses in the other laterally extending flange with said projection being adapted to snap into a selected angularly spaced recess to retain said insert selectively in said one portion and said another position.

2. Apparatus as defined in claim 1 in which said angularly spaced recesses are in the flange carried by said first portion of said elongated member and said projection is mounted on the flange carried by said insert.

* * * * *